United States Patent [19]

Nakashima et al.

[11] 4,287,177

[45] Sep. 1, 1981

[54] WOUND COVERING MATERIAL

[75] Inventors: Toshihide Nakashima, Kurashiki; Osamu Nakaji, Sakura; Koichi Takakura, Okayama; Takayoshi Suzuki, Suita, all of Japan

[73] Assignees: Kuraray Co., Ltd., Kurashiki; Yamanouchi Pharmaceutical Co., Ltd., Tokyo, both of Japan

[21] Appl. No.: 66,699

[22] Filed: Aug. 15, 1979

[30] Foreign Application Priority Data

Aug. 18, 1978 [JP] Japan ............................... 53-101267

[51] Int. Cl.³ ............................................. A61K 31/78
[52] U.S. Cl. ............................. 424/81; 424/DIG. 13
[58] Field of Search ........................................... 424/81

[56] References Cited

U.S. PATENT DOCUMENTS

| 3,575,946 | 4/1971 | Chromelek et al. | 260/86.1 |
| 3,577,516 | 5/1971 | Gould et al. | 424/33 X |
| 3,868,447 | 2/1975 | Kiment | 424/81 |
| 3,963,685 | 6/1976 | Abrahams | 424/81 X |

*Primary Examiner*—Leonard Schenkman
*Attorney, Agent, or Firm*—Oblon, Fisher, Spivak, McClelland & Maier

[57] ABSTRACT

The present invention provides a covering material consisting essentially of a hydrophilic, water insoluble polymer (component A), a high boiling plasticizer and/or organic solvent (component B) for said component A, and an aqueous liquid (component C). Said covering material is useful as a protective covering material for forming a film or coat on the skin and/or wound surface in the treatment of burn. The material is characterized in that film or coat formation on the skin and/or wound surface can be realized in a short time.

18 Claims, No Drawings

WOUND COVERING MATERIAL

BACKGROUND OF THE INVENTION

1. Field of the Invention

This invention relates to a covering material and more specifically to a protective covering material for forming a film or coat on the skin or wound surface.

2. Description of the Prior Art

It is effective in the treatment of wounds, especially burn, to cover the wound surface with a membranous protective covering material so that intrusion of bacteria from without, hence bacterial infection through the wound surface, may be inhibited. For practical purposes, such as covering material is required to be (i) non-irritating and nontoxic to the skin or wound, (ii) permeable to the exudate from the burnt skin to the extent that the exudate may not accumulate beneath the covering coat, (iii) not sticking to the wound surface, and (iv) easily removable, when necessary.

As a covering material having such characteristics, there is known a plastisol consisting of a hydrophilic, water insoluble polymer powder and a high boiling plasticizer or solvent therefor (U.S. Pat. No. 3,577,516). This materials, as is disclosed in said U.S. patent, is applied to the skin to be protected in the following way: First, the liquid, high boiling plasticizer (or solvent) is applied to the skin by spraying, and then the polymer powder is sprayed onto that skin. By this procedure, the polymer powder and the high boiling plasticizer (or solvent) are mixed on the skin and give a plastisol, which forms a film to protect the skin. However, in using such a plastisol in the field of clinical medicine, for example in the treatment of thermal burn, the time required for formation of such a plastisol film on the skin becomes a problem. In the case of the covering material disclosed in the above-cited U.S. patent, it takes about 30 minutes to form a film thereof on the skin, while the clinician cannot do subsequent treatments but have to wait for completion of the film formation. Therefore, such a covering material has been thought to be unfavorable and some measure for reducing the film formation time has been waited for.

SUMMARY OF THE INVENTION

Therefore, an object of the invention is to provide a protective covering material which forms a film or coat on the skin or wound surface and thereby inhibits intrusion of bacteria from without, said protective covering material having the desired characteristics (i) to (iv) mentioned above and at the same time being capable of forming a film in a shorter period of time.

Another object of the invention is to provide a covering material to be used in other various fields where a shortened film formation time is required.

Further objects of the invention will become clear from the following detailed description of the invention.

These objects can be achieved by providing a protective covering material for forming a film on the skin and/or wound surface, which comprises a hydrophilic, water insoluble polymer (component A) and a high boiling plasticizer and/or organic solvent (component B) for said component A and is characterized by the use of an aqueous liquid (component C). Such a protective covering material may be used as a covering material for other various fields.

DETAILED DESCRIPTION OF THE PREFERRED EMBODIMENTS

The polymer (component A) to be used in practicing the present invention may be any of those hydrophilic, water insoluble polymers that have good biocompatibility and are capable of absorbing water in amounts of more than 10% by weight, preferably more than 20% by weight, (the water absorbing power being measured at 37° C. and being calculated by the formula: "the amount of water contained in, i.e. absorbed by, the polymer"/"the weight of the dry polymer" × 100). Polymers derived from hydroxy-lower alkyl acrylates or hydroxy-lower alkyl methacrylates, however, are preferred because of their good compatibility and film-forming property. In more detail, such hydroxy-lower alkyl (meth)acrylate polymers are the polymers obtained from a monomer represented by the general formula

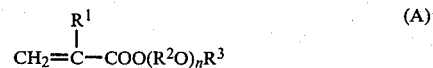

wherein $R^1$ is H or methyl, $R^2$ is alkylene containing 2–5 carbon atoms, n is 1–30, and $R^3$ is H, alkyl of 1–3 carbon atoms, or $C_2$ or $C_3$ alkyl substituted by such a polar substituent as amino or alkoxy of 1–3 carbon atoms, with said monomer amounting to at least 67% by weight, preferably 75% by weight or more, of the monomers constituting the polymer. Examples of the monomer represented by formula (A) are hydroxyethyl acrylate, hydroxyethyl methacrylate, hydroxy-isopropyl acrylate, hydroxy-isopropyl methacrylate, hydroxy-n-butyl acrylate, hydroxy-n-butyl methacrylate, hydroxy-n-hexyl acrylate, hydroxy-n-hexyl methacrylate, diethylene glycol monoacrylate, diethylene glycol monomethacrylate, dipropylene glycol monoacrylate, dipropylene glycol monomethacrylate, polyethylene glycol (n=30) acrylate, polyethylene glycol (n+30) methacrylate, polypropylene glycol (n=30) acrylate, polypropylene glycol (n=30) methacrylate, methoxyethyl methacrylate, ethoxyethyl methacrylate, n-propoxyethyl methacrylate, aminoethoxyethyl methacrylate, aminopropoxyethyl methacrylate, methoxyethoxyethyl methacrylate, ethoxyethoxyethyl methacrylate, propoxyethoxyethyl methacrylate, methoxypropoxyethyl methacrylate, ethoxypropoxyethyl methacrylate, and propoxypropoxyethyl methacrylate. The most preferred is hydroxyethyl methacrylate. The hydroxy-lower alkyl (meth) acrylate polymers can be obtained not only by homopolymerizing a single monomer as mentioned above, but also by copolymerizing two or more of the above-mentioned monomers.

Further, the above-mentioned polymer may also be obtained by copolymerizing a monomer or monomers represented by formula (A) and some other copolymerizable monomer or monomers not covered by formula (A) in an amount not exceeding 33% by weight, preferably not exceeding 25% by weight, so that a water-absorbing polymer as mentioned above may be obtained. The copolymerizable monomer may be, for example, acrylic acid, methacrylic acid, N-vinylpyrrolidone, acrylamide or methacrylamide. However, the use is preferred of a hydrophobic monomer represented by the formula.

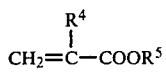

(B)

wherein $R^4$ is H or methyl and $R^5$ is alkyl of 1–4 carbon atoms. Examples of the monomer represented by formula (B) are methyl acrylate, ethyl acrylate, isopropyl acrylate, n-butyl acrylate, methyl methacrylate, ethyl methacrylate, isopropyl methacrylate and n-butyl methacrylate. Among others, methyl methacrylate is preferable. These copolymerizable monomers may be used either alone or in combination of two or more thereof, in an amount within the range mentioned above.

Among polymers obtainable by using the above-mentioned monomers, homopolymers of monomers represented by formula (A) and copolymers of two or more monomers each represented by formula (A) are preferably used for the purpose of obtaining highly transparent covering materials. Especially, poly (hydroxyethyl methacrylate) is desirable for that purpose. For obtaining protective covering materials favorable in respect to inhibition of exudation of blood components, especailly blood proteins, the use is preferred of copolymers of monomers represented by formula (A) and monomers represented by formula (B) with monomer (B) contents of not more than 33% by weight, preferably 10–25% by weight. Especially, hydroxyethyl methacrylate-methyl methacrylate copolymers are desirable. Whereas selection of suited polymers can be made depending on the respective uses of the covering materials, poly(hydroxyethyl methacrylate) can most generally be used. The polymerization degree of the polymers is not particularly restricted, but generally it is in the range of 100–10,000.

It is preferable from the viewpoint of film-forming property that these polymers are substantially uncrosslinked polymers. The term "substantially uncrosslinked polymers" used herein means those polymers that are soluble in solvents and are not three-dimentional.

Such substantially uncrosslinked polymers can be prepared in a manner easy to those skilled in the art. When hydroxyethyl methacrylate is used as a monomer, however, care should be taken, since the monomer usually contains ethylene glycol dimethacrylate which is a cross-linking monomer. Typical methods of polymerizing hydroxyethyl methacrylate are, for example, (1) the one according to the disclosure of U.S. Pat. No. 3,575,946 which comprises effecting solution polymerization in an organic solvent such as dimethyl sulfoxide, dimethylformamide, methanol or ethanol, (2) the one comprising recovering the polymer from the polymerization mixture after the above-mentioned solution polymerization either by coagulation thereof in water or by removing the organic solvent by evaporation, and (3) the one disclosed in U.S. Pat. No. 3,963,685, which comprises carrying out polymerization in aqueous phase using sufficiently purified hydroxyethyl methacrylate with a very small crosslinking monomer content (not more than 0.035% by weight). Other methods may also be mentioned, such as the usual one comprising subjecting the polymerization mixture after the above-mentioned solution polymerization to precipitation in an organic nonsolvent such as benzene, by which, however, the polymer obtained is slightly inferior in film-forming ability to those obtained by the previously mentioned methods. In the present invention, the polymers so prepared are pulverized and used in the form of powders which pass a Tyler's 100-mesh standard sieve (polymer particles having diameters of not more than 149 microns), preferably a 200-mesh Tyler sieve (particle sizes being not more than 74 microns). Whereas, for the purpose of obtaining larger polymer surface areas and making easier the contact with the high boiling plasticizer or the like, it is preferred to pulverize the polymers to particle sizes below 10 microns, such finely pulverized powders have a disadvantage that, in application to the skin, they can easily be scattered around. Generally, therefore, the polymers are pulverized to the extent that they can pass a 200-mesh sieve.

As the high boiling plasticizer or organic solvent (component B, hereinafter called "plasticizer or the like") for the above-mentioned polymer to be used in this invention may be any of those that have boiling points of 120° C. or above, are nontoxic and non-irritating to the human body and can plasticize or dissolve the above-mentioned polymers to be used in this invention. The reason for preference of the plasticizer or the like having a boiling point of 120° C. or above is that, when the plasticizer or the like is applied to the skin or wound surface together with the polymer mentioned above and a film or coat is formed, the plasticizer or the like can hardly evaporate so that stiffening and embrittlement of the film otherwise caused by evaporation of the plasticizer or the like may be prevented. Such a plasticizer or the like includes propylene glycol, trimethylene glycol, 1,3-butanediol, 1,4-butanediol, 2,5-hexanediol, 2-methyl-2,4-pentanediol, 2,4-heptanediol, 2-ethyl-1,3-hexanediol, diethylene glycol, triethylene glycol, tetraethylene glycol, higher polyethylene glycols (e.g. hydroxy-terminated ethylene oxide polymers having average molecular weights of 200–6,000), dipropylene glycol, tripropylene glycol and other glycols such as polypropylene glycols having molecular weights of not more than 900, propylene glycol monoethyl ether, monoacetin, tri (hydroxyethyl) citrate, di(hydroxypropyl) oxalate, hydroxypropyl acetate, glycerol triacetate, glycerol tributyrate, liquid sorbitol-ethylene oxide adducts, liquid glycerol-ethylene oxide adducts, diethylene glycol monomethyl ether, diethylene glycol monoethyl ether, diethylene glycol diacetate and other water soluble polar compounds. Among others, polyethylene glycol, $HO(CH_2CH_2O)_nH$ (n>1), is preferred, desirably the one having a molecular weight of 800 or less, more preferably 200–600, from the viewpoints of film-forming property and toxicity.

A special feature of the invention consists in that, in forming a film or coat on the skin or wound surface, an aqueous liquid is used in addition to the above-mentioned two components, polymer and plasticizer or the like. The term "aqueous liquid" used herein means water which may contain an electrolyte such as sodium chloride in such an amount that the resulting solution is isotonic to or hypotonic than the blood. Generally, however, distilled water or physiological saline is used as such aqueous liquid. Surprisingly, the use of the aqueous liquid in forming on the skin or wound surface a film from the protective covering material consisting of the above-mentioned polymer and plasticizer or the like can bring dramatic reduction in film formation time to one third to one tenth compared with the cases of conventional materials. Such a significant effect, which is very important in cases where a film is formed on a wound surface, is thought to be brought about by the fact that the addition of the aqueous liquid causes increase in solubility of the above-mentioned polymer, decrease in viscosity of the plasticizer or the like resulting in enhanced penetration of the plasticizer or the like into the polymer particles, increase in rate of swelling of the polymer particles, and so on.

The ratio of the plasticizer or the like plus aqueous liquid (hereinafter combinedly called "liquid component") to the polymer is generally such that the polymer amounts to 20–80% by weight and the liquid component to 80–20% by weight, preferably such that they are approximately equal in amount. While the optimal ratio of the aqueous liquid to the liquid component can be selected depending upon the kinds of the polymer and the plasticizer or the like, generally the aqueous liquid is used in an amount of 20–70% by weight, preferably 30–60% by weight. With a smaller amount of the aqueous liquid than 20% by weight, the effect of reduction in film formation time is slight, and conversely, with a larger amount than 70% by weight, the strength of the film formed is low, and with a too excessive amount any film will not form.

The above-mentioned components, polymer, plasticizer or the like and aqueous liquid, when applied on the skin or wound surface, form a film thereon. Therefore, these components are generally blended by the surgeon prior to use thereof in medical treatment. It is necessary that the protective covering material of the present invention be supplied to the user, a surgeon, for instance, in such a manner that the polymer powder and the plasticizer or the like are packed in separate containers. The aqueous liquid may either be mixed with the plasticizer or the like and packed in one and the same container or be packed in a separate container from the one for the plasticizer or the like. The aqueous liquid may also be mixed with the plasticizer or the like just prior to application of the above-mentioned polymer and plasticizer or the like to the skin.

Methods of applying the above-mentioned components, polymer powder, plasticizer or the like and aqueous liquid, to the skin or wound surface will now be described.

First of all may be mentioned a method according to which the plasticizer or the like and the aqueous liquid are applied to the skin or wound surface separately, or preferably in admixture, and then the above-mentioned polymer powder is apllied thereupon. According to another method, the polymer powder, plasticizer or the like and aqueous liquid are applied to the skin or wound surface simultaneously. Here, each component is applied to the skin or wound surface by spraying or by spreading by the aid of a syringe tube. For spraying, methods as disclosed in U.S. Pat. No. 3,577,516 are applicable in the present invention, too. The polymer powder applied to the skin or wound surface is swelled with or dissolved in the liquid component and forms a stable film or coat in a short time, which adheres to the skin or wound surface. The term "film or coat" used herein means a plastisol film formed by mutual adhesion of the polymer particles swollen with the liquid component or a membrane formed as a result of dissolution of the polymer powder. It is preferable to apply the polymer powder and the liquid component to the skin or wound surface alternately several times so that a sufficiently thick protective film may be obtained. Generally, film thickness of about 10–1,000 microns is preferred.

The protective covering material of the present invention is useful as a covering material not only for wounds of the skin by heat but also for traumas such as incised wounds and abrasions. It is also effective as a covering material for maintaining cleanliness of operation sites before and after operation, as a protective covering material for the site from which a piece of skin has been cut, or as a protective covering material for bedsores.

The protective covering material of the present invention may contain, in addition to the above three components, other necessary and appropriate components such as a medicinally active component.

The following examples illustrate the invention in more detail. The examples, however, should by no means be construed as limiting the invention.

EXAMPLE 1

A liquid mixture (liquid component) of polyethylene glycol having a number average molecular weight of 400 ("Macrogolum 400" by trade name, manufactured by Maruishi Pharmaceutical Co., Ltd.) and distilled water (the mixing ratio being given in Table 1) was applied thinly to a glass plate by spraying, and over this liquid layer was dusted uniformly in an amount equal by weight to that of the liquid mixture a powder (passing a 200-mesh sieve) of soluble poly(hydroxyethyl methacrylate) having an intrinsic viscosity in dimethylformamide $[\eta] = 1.65$ dl/g (30° C.), a water absorption capacity of 61% (37° C.) and a packing density of 0.77 g/cc, and the resulting layer was allowed to stand. The film formation time (time required for a film to be formed) was measured by picking up one end of the mixture on the glass plate with a pair of tweezers at intervals, and then the peelability time (time required for formation of a uniform film having a strength such that it does not break on peeling) was measured by examining whether the film could be peeled off with a pair of tweezers. The results are shown in Table 1. It is clear from the results that sharp reduction in film formation time can be attained according to the invention.

TABLE 1

| Specimen No. | Amount of water in liquid component (% by weight) | Film formation time (min.) | Peelability time (min.) |
| --- | --- | --- | --- |
| 1 | 0 | 12–13 | 25 |
| 2 | 20 | 5–6 | 10 |
| 3 | 40 | 3 | 5 |
| 4 | 60 | 1 | 1 |
| 5 | 80 | — | — |

Note:
With 80% by weight of water, film formation was impossible.

In the following are shown the results of certain tests concerning practical use of the protective covering material of the present invention formed by addition of an aqueous liquid. The powder was sterilized with ethylene oxide gas and the liquid component by heating.

(i) Safety

Employing two compositions shown in Table 1 in lines for specimens Nos. 3 and 4, respectively, films were made each having a thickness of about 0.6 mm and tested, according to general testing method 39, testing of plastic containers for transfusion fluids, for (6) acute toxicity, (7) intracutaneous reaction, (8) pyrogenicity, (9) hemolysis and (10) implantation test, Japanese Pharmacopeia, 9th edition. The results are shown in Table 2.

Either of the specimens did not show any abnormality.

TABLE 2

| Test for | Specimen No. | Results |
|---|---|---|
| Acute toxicity | 3 | No abnormality, no death |
| | 4 | " |
| Intracutaneous reaction | 3 | No erythema, no edema, no hemorrhage and no necrosis |
| | 4 | No erythema, no edema, no hemorrhage and no necrosis |
| Pyrogen | 3 | Not positive |
| | 4 | " |
| Hemolysis | 3 | No hemolysis |
| | 4 | " |
| Implantation | 3 | No hemorrhage, no encapsulation and no other abnormalities |
| | 4 | No hemorrhage, no encapsulation and no other abnormalities |

(ii) Primary skin irritation

Eight albino rabbits with sheared backs were divided into two subgroups, the backs of 4 animals were shaved, and using a sterilized 18G needle an injury in the form of parallel crosses was given to the horny layer of the sheared backs of 4 animals and of the shaved backs of 4. Two groups each of 8 such experimental animals were prepared. Employing the composition shown in Table 1 for specimen No. 1, 0.25 g of the liquid component was dropped from a syringe tube onto the injured site of each of Group 1 animals and spread to a size about 2.5 cm×2.5 cm. Thereupon was dusted 0.25 g of the powder to form a film. Ten minutes later, 4 sheets of gauze were applied and fixed with an elastic bandage. Group 2 animals were treated by the above procedure but employing the composition No. 3 in Table 1.

Twenty-four hours later, the bandage was removed, and peelability (easiness of separation) of the gauze from the film was evaluated for each animal. In the case of specimen No. 1, the lowest sheet of gauze was adhering to the film, whereas in the case of specimen No. 3, the gauze could easily be separated from the film. Then, a wad of absorbent cotton sufficiently impregnated with 0.9% physiological saline solution was applied to the film for 10 minutes to remove the film, and the skin that had been beneath the film was observed for erythema and/or crust formation and edema, revealing no abnormality at all. Subsequent two observations made 48 and 72 hours later, respectively, could not reveal any abnormality at all, either. It was thus confirmed that neither of specimens Nos. 1 and 3 did not cause any primary skin irritation.

(iii) Inhibition of bacterial intrusion in vitro

A standard agar medium was placed in a glass dish, and thereon was formed a film having a thickness of about 0.1 mm by spraying the liquid component and the powder. The weight ratio of the liquid component to the powder was 1:1. The liquid component had the composition of specimen No. 1, 2, 3 or 4 in Table 1. Further on the film, a suspension of *Escherichia coli* or *Pseudomonas aeruginosa* in physiological saline was spread and incubated at 37° C. for 24 hours. A disk-like specimen, 7.5 mm in diameter, was taken and the number of bacteria above the film and that beneath the film were determined separately. The results, shown in Table 3, proved that all of the compositions could inhibit penetration of bacteria.

TABLE 3

| Specimen No. | Bacterium | Number of bacteria Above the film | Number of bacteria Beneath the film |
|---|---|---|---|
| 1 | E. coli | $10^8$ | No bacteria detected |
| | P. aer. | $10^7$ | " |
| 2 | E. coli | $10^7$ | " |
| | P. aer. | $10^7$ | " |
| 3 | E. coli | $10^8$ | " |
| | P. aer. | $10^8$ | " |
| 4 | E. coli | $10^8$ | " |
| | P. aer. | $10^8$ | " |

(iv) Inhibition of bacterial intrusion in animal experiment

Second degree burn was provided on the shaved backs of rats using boiling water to the extent that about 10% of the body surface area was injured. Four groups each of 3 rats were prepared. One group, which was the control group, was not treated any longer. In the remaining three groups, film formation was effected by spraying the liquid component and powder, employing the liquid component compositions of specimens Nos. 2, 3 and 4 in Table 1, respectively. Onto the film or directly onto the burn was poured 0.1 ml of a culture solution of *P. aeruginosa*, containing $10^7$ bacteria. After 7 days of feeding, the fascia under the film was taken and disperesed uniformly, and the number of bacteria was determined. The results are shown in Table 4. It was confirmed that the film formed by spraying the liquid component and powder could inhibit penetration of bacteria.

TABLE 4

| Specimen No. | Number of bacteria | | |
|---|---|---|---|
| 2 | 0, | 0, | 0 |
| 3 | 0, | 0, | 0 |
| 4 | 0, | 0, | 0 |
| Control (without spraying of liquid component-powder) | $10^7$, | $10^6$, | $10^7$ |

As stated above, it has been established that the covering material of the present invention is safe and effective as a covering material for wounds. The following description shows the results of application of the covering material of the invention to a human body.

A second degree burn on the forearm covering about 5% of the body surface area was sprayed first with the liquid component of specimen No. 3 in Table 1 and then with the previously mentioned soluble poly(hydroxyethyl methacrylate) powder uniformly. These sprayings were repeated three times, and 10 minutes later, the resulting film was fixed with gauze and bandage. There was no complaint of painful irritation to the affected part and no accumulation of the exudate beneath the film. Observation after 7 days revealed good healing and no infection. Change of the gauze and bandage was made daily. Because there was no sticking of the gauze to the film, no complaint of pain was received and observation of the wound area through the film was easy at the time of said change. As a control experiment, a similar second degree burn on the forearm covering about 5% was sprayed with the liquid component of specimen No. 1 in Table 1 and with the powder each three times and treated as above. Although the process of healing was approximately similar to the above case, the lowest gauze layer was firmly adhering to the film and consequently the affected part under treatment could not be observed.

EXAMPLE 2

Mixtures of various kinds of plasticizer or the like specified in Table 5 and distilled water were each applied thinly to a glass plate by the procedure of Example 1, then the same poly(hydroxyethyl methacrylate) as in Example 1 in the form of a powder passing a 200-mesh sieve was dusted thereover, and the resulting layer was allowed to stand. The film formation time and peelability time were measured by the procedure of Example 1. The results are shown in Table 5.

TABLE 5

| Plasticizer or the like | Content of distilled water in liquid component (% by weight) | Film formation time (min.) | Peelability time (min.) |
| --- | --- | --- | --- |
| Polyethylene glycol (mol. wt. = 200) | 0 | 6 | 10.5 |
| | 40 | 1.5 | 5 |
| Polyethylene glycol (mol. wt. = 400) | 0 | 13 | 25 |
| | 40 | 3 | 5 |
| Polyethylene glycol (mol. wt. = 600) | 0 | 22 | 60 |
| | 40 | 1.5 | 4 |

Notes:
Polyethylene glycol (mol. wt. = 200): manufactured by Kishida Chemical Co., Ltd.
Polyethylene glycol (mol. wt. = 400): manufactured by Nakarai Chemical Co., Ltd.
Polyethylene glycol (mol. wt. = 600): manufactured by Nikka Seiko Co., Ltd.

EXAMPLE 3

A liquid mixture (liquid component) of polyethylene glycol having a number average molecular weight of 400 and distilled water (the mixing ratio being shown in Table 6) was applied thinly to a glass plate by the procedure of Example 1. A powder passing a 200-mesh sieve of soluble hydroxyethyl methacrylate-methyl metacrylate copolymer (the monomer ratio being 8:2 by weight) having an intrinsic viscosity in demthylformamide $[\eta]=0.95$ dl/g (30° C.), a water absorbing powder of 49% (37° C.) and a packing density of 0.68 g/cc was dusted uniformly over the liquid layer in an amount equal in weight to that of the liquid component. The whole system was allowed to stand, and the film formation time was measured by the method used in Example 1. The results are shown in Table 6.

TABLE 6

| Content of distilled water liquid component (% by weight) | Film formation time (minutes) |
| --- | --- |
| 0 | 30 |
| 40 | 4 |
| 80 | —* |

*Any film could not be formed.

What is claimed is:

1. A protective covering material for forming a film or coat on skin and/or wound surfaces consisting essentially of a hydrophillic, water-insoluble and substantially uncrosslinked polymer in powder form (component A), polyethylene glycol (component B) and an aqueous liquid (component C), wherein said polymer of component A is derived from a monomer represented by the formula:

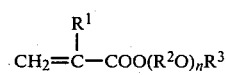

wherein $R^1$ is H or methyl, $R^2$ is alkylene containing 2–5 carbon atoms, $R^3$ is H, alkyl containing 1–3 carbon atoms or $C_2$- or $C_3$-alkyl substituted by amino or alkoxy of 1–3 carbon atoms and n is 1–30, at least 67% by weight of said polymer being composed of said monomer, wherein said component A amounts to 20–80% by weight of components A+B+C, said components B+C together amount to 80–20% by weight of components A+B+C, and said components C amounts to 20–70% by weight of components B+C.

2. A protective covering material as claimed in claim 1, wherein said polymer of component A is a polymer containing hydroxyethyl methacrylate as a constituent thereof.

3. A protective covering material as claimed in claim 2, wherein said polymer is poly(hydroxyethyl methacrylate).

4. A protective covering material as claimed in claim 1, wherein said component A is a copolymer of
   (a) 75–90 parts by weight of a monomer represented by the formula:

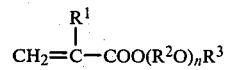

wherein $R^1$ is H or methyl, $R^2$ is alkylene containing 2–5 carbon atoms, $R^3$ is H, alkyl of 1–3 carbon atoms, or $C_2$- or $C_3$-alkyl substituted by amino or alkoxy of 1–3 carbon atoms and n is 1–30, and
   (b) 25–10 parts by weight of a monomer represented by the formula:

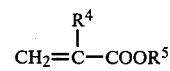

wherein $R^4$ is H or methyl and $R^5$ is alkyl of 1–4 carbon atoms.

5. A protective covering material as claimed in claim 4, wherein said copolymer is a copolymer of hydroxyethyl methacrylate and methyl methacrylate.

6. A protective covering material as claimed in claim 1, wherein said component B is polyethylene glycol having a molecular weight of 800 or less.

7. A protective covering material as claimed in claim 1, wherein said component C is distilled water.

8. A protective covering material as claimed in claim 1, wherein said component C is physiological saline.

9. A protective covering material as claimed in claim 1, wherein said component C amounts to 30–60% by weight of components B+C.

10. A method of forming a film or coat on skin and/or wound surfaces, which comprises applying polyethylene glycol (component B) together with an aqueous liquid (component C), either separately or in admixture and then applying thereto a hydrophilic, water-insoluble and substantially uncrosslinked polymer in powder form (component A) so that a film or coat may be formed on said skin and/or wound surfaces, wherein said polymer of component A is derived from a monomer represented by the formula:

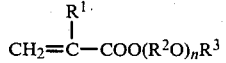

wherein $R^1$ is H or methyl, $R^2$ is alkylene containing 2-5 carbon atoms, $R^3$ is H, alkyl containing 1-3 carbon atoms or $C_2$- or $C_3$-alkyl substituted by amino or alkoxy of 1-3 carbon atoms and n is 1-30, at least 67% by weight of said polymer being composed of said monomer, wherein said component A amounts to 20-80% by weight of components A+B+C, said components B+C together amount to 80-20% by weight of components A+B+C, and said component C amounts to 20-70% by weight of components B+C.

11. A method as claimed in claim 10, wherein said polymer of component A is a polymer containing hydroxymethyl methacrylate as a constituent thereof.

12. A method as claimed in claim 11, wherein said polymer is poly(hydroxyethyl methacrylate).

13. A method as claimed in claim 10, wherein said component A is a copolymer of
(a) 75-90 parts by weight of a monomer represented by the formula:

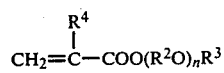

wherein $R^1$ is H or methyl, $R^2$ is alkylene containing 2-5 carbon atoms, $R^3$ is H, alkyl of 1-3 carbon atoms, or $C_2$- or $C_3$-alkyl substituted by amino or alkoxy of 1-3 carbon atoms and n is 1-30, and
(b) 25-10 parts by weight of a monomer represented by the formula:

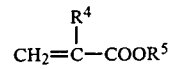

wherein $R^4$ is H or methyl and $R^5$ is alkyl of 1-4 carbon atoms.

14. A method as claimed in claim 13, wherein said copolymer is a copolymer of hydroxyethyl methacrylate and methyl methacrylate.

15. A method as claimed in claim 10, wherein said component B is polyethylene glycol having a molecular weight of 800 or less.

16. A method as claimed in claim 10, wherein said component C is distilled water.

17. A method as claimed in claim 10, wherein said component C is physiological saline.

18. A method as claimed in claim 10, wherein said component C amounts to 30-60% by weight of components B+C.

* * * * *

UNITED STATES PATENT AND TRADEMARK OFFICE
CERTIFICATE OF CORRECTION

PATENT NO. : 4,287,177
DATED : Sep. 1, 1981
INVENTOR(S) : Nakashima et al

It is certified that error appears in the above—identified patent and that said Letters Patent is hereby corrected as shown below:

In Column 2, Line 45:

"n+30" should read --n=30--

Signed and Sealed this

Twenty-seventh Day of April 1982

[SEAL]

Attest:

GERALD J. MOSSINGHOFF

Attesting Officer

Commissioner of Patents and Trademarks